(12) United States Patent
Bache et al.

(10) Patent No.: US 10,271,968 B2
(45) Date of Patent: Apr. 30, 2019

(54) KNITTED INTERFACE (71) Applicant: Ossur Iceland ehf, Reykjavik (IS)

(72) Inventors: Andrew Bache, Reykjavik (IS);
Christophe Valois, Reykjavik (IS);
Magnus Oddsson, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 79 days.

(21) Appl. No.: 15/219,772

(22) Filed: Jul. 26, 2016

(65) Prior Publication Data

US 2017/0027719 A1 Feb. 2, 2017

Related U.S. Application Data

(60) Provisional application No. 62/197,118, filed on Jul. 27, 2015.

(51) Int. Cl.
*A61F 2/78* (2006.01)
*D04B 1/16* (2006.01)
*D04B 1/18* (2006.01)
*D04B 1/22* (2006.01)

(52) U.S. Cl.
CPC .............. *A61F 2/7812* (2013.01); *D04B 1/16* (2013.01); *D04B 1/18* (2013.01); *D04B 1/22* (2013.01); *A61F 2002/7818* (2013.01)

(58) Field of Classification Search
CPC .............. D04B 1/16; D04B 1/18; D04B 1/22
USPC .......................................... 442/308, 309, 312
See application file for complete search history.

(56) References Cited

U.S. PATENT DOCUMENTS

| | | | |
|---|---|---|---|
| 4,840,635 | A | 6/1989 | Smith et al. |
| 4,923,474 | A | 5/1990 | Klasson et al. |
| 5,505,692 | A | 4/1996 | Cho |
| 5,571,208 | A | 11/1996 | Caspers |
| 5,890,380 | A | 4/1999 | Ives et al. |
| 6,440,172 | B1 | 8/2002 | Davant, Jr. et al. |
| 6,516,637 | B1 | 2/2003 | Fancher et al. |
| 6,706,364 | B2 | 3/2004 | Janusson et al. |
| 6,871,516 | B2 | 3/2005 | Peeler et al. |

(Continued)

FOREIGN PATENT DOCUMENTS

| | | |
|---|---|---|
| CN | 2921050 Y | 7/2007 |
| DE | 3307586 U1 | 8/1993 |

(Continued)

OTHER PUBLICATIONS

Roy, Manas Datta and Sujit Kumar Sinha. "Performance of Wicking through Yarn and Fabric Made from Polyester Fibres of Different Cross-sections." International Journal of Textile Science 3(3). (2014): 44-50. Print. (Year: 2014).*

(Continued)

*Primary Examiner* — Jenna L Johnson
(74) *Attorney, Agent, or Firm* — Workman Nydegger (57) ABSTRACT

A knitted interface comprises a knitted structure formed from a plurality of elastomeric polymer filaments having a plurality of interstices permitting a transfer of air therethrough. The elastomeric polymer filaments may have a solid or hollow cross-section. The interstices vary in shape and size according to a knit density of the knitted structure upon movement or radial distension of the knitted interface. The elastomeric polymer filaments may be made from silicone.

19 Claims, 4 Drawing Sheets

(56) References Cited

U.S. PATENT DOCUMENTS

| | | |
|---|---|---|
| 7,459,598 B2 | 12/2008 | Sigurjonsson et al. |
| 8,317,873 B2 | 11/2012 | Doddroe et al. |
| 8,425,441 B2 | 4/2013 | Ingimundarson |
| 8,523,951 B2 | 9/2013 | Kania |
| 9,050,201 B2 | 6/2015 | Egilsson et al. |
| 2003/0181989 A1 | 9/2003 | Eberle et al. |
| 2003/0213269 A1 | 11/2003 | Peeler et al. |
| 2011/0202018 A1 | 8/2011 | Dias et al. |
| 2012/0054945 A1 | 3/2012 | Grubisha |
| 2012/0110713 A1 | 5/2012 | Hirtz |
| 2014/0025183 A1 | 1/2014 | Kelley et al. |
| 2014/0180182 A1 | 6/2014 | Collins et al. |
| 2017/0216058 A1 * | 8/2017 | Dias ...................... A61F 2/7812 |

FOREIGN PATENT DOCUMENTS

| | | | |
|---|---|---|---|
| DE | 20205706 U1 | 7/2002 | |
| WO | 2012160307 A1 | 11/2012 | |
| WO | WO-2012160307 A1 * | 11/2012 | ............. D04B 21/18 |
| WO | 2015094385 A1 | 6/2015 | |

OTHER PUBLICATIONS

International Search Report from PCT Application No. PCT/US2016/044036, dated Oct. 6, 2016.

* cited by examiner

KNITTED INTERFACE

FIELD OF THE DISCLOSURE

This disclosure relates to a prosthetic or orthopedic interface, including a knitted structure formed by elastomeric filaments.

BACKGROUND

Prosthetic or orthopedic interfaces typically interact with a patient's body, and may be in direct contact with the skin. These interfaces can cause irritation and pain if not interfaced properly with the wearer's skin. Rigid devices such as neck and back braces or casts can create pressure sores and chaffing, while less rigid devices, such as bandages and wraps, may suffer from poor breathability or cause skin irritation.

Numerous liners or paddings are employed in prosthetic and orthopedic systems, and serve as an interface between a corresponding device and the body of the wearer. For example, in prosthetic devices, a suspension liner is generally understood as a sleeve worn over a post-operative stump or limb that serves as the interface between the limb and prosthesis or a prosthetic device, such as a hard socket. These liners are typically made of an air impermeable elastomer material, such as silicone. The liners may comprise a single layer or multiple layers, with different layers providing different benefits to the wearer. Examples include U.S. Pat. No. 4,923,474 granted May 8, 1990, U.S. Pat. No. 6,706,364, granted Mar. 16, 2004, and U.S. Pat. No. 9,050,201, granted Jun. 9, 2015, each incorporated herein by reference.

Liners are used traditionally to provide cushioning to a residual limb by distributing pressure on the limb caused by a prosthetic device. The liner also protects the limb from irritation that might be caused by movement of the prosthesis against the limb. Absent a liner, the prosthesis will directly contact the skin. Any movement or slippage of the prosthesis at the interface with the limb will therefore result in friction between the prosthesis and limb and, irritation to the limb. Presence of the liner between the limb and the prosthesis eliminates this problem by serving as a protective barrier between the limb and the prosthesis; movement at the interface with the limb will be borne by the liner and not the limb.

Some users find known liners to be uncomfortable for several reasons, including poor pressure distribution resulting from the limb-liner-socket interface. When using a prosthetic socket, normal and shear forces are generated upon the skin of the residual limb. Many known liners fail to distribute pressure evenly about the residual limb, causing areas of the limb to be subject to pressure greater than others. The concentrated pressure areas can cause discomfort, pain, and pressure marks.

In another form, the interface may be used interchangeably with a spacer element, as taught and discussed in U.S. Pat. No. 8,425,441, granted Apr. 23, 2013, and incorporated herein by reference. According to this embodiment, a spacer element or liner is a compressive pad along a frame for an orthopedic device, thereby serving as an interface between a rigid or semi-rigid frame and the limb of the user.

Another interface feature that provides comfort is breathability. Many known interfaces are made of materials that do not breathe or wick moisture away from the residual limb when donned. Without a breathable interface, moisture and heat buildup on the surface of the skin. Excess moisture may create foul odors, and cause chaffing and irritation. The raised surface temperature of the skin increases the temperature of the interface and changes its material properties.

Users also find many known interfaces difficult to don and doff. Liners may be found too thick or inflexible, making them hard to don and doff because they are inflexible or there is too much friction between the skin and the liner.

SUMMARY

The present disclosure is directed to orthopedic and prosthetic interfaces, preferably in the form of a liner, that may be arranged to be durable, breathable, distribute pressure evenly across a limb, minimize shear stresses, be easy to don and doff, and provide comfort to the wearer. Generally, the interface is formed by knitting, purling, weaving or crocheting using one or more long extrusions of an elastomeric polymer. This structure is ideally suitable as a prosthetic liner, sleeve, pad or combination in orthopedic or prosthetic applications as it both "breathes" and contains excellent soft tissue loading properties.

In an exemplary embodiment of an interface, a suspension liner comprises a tubular structure knitted from elastomeric filaments. The elastomeric filaments may be silicone or other suitable polymeric material, and the filaments may be solid or hollow. In a variation, the filaments used to knit the liner may be a composite filament, wherein the filaments are a combination of at least one elastomeric material and at least one fabric-textile material.

The stitch density may vary, whereby some sections of the liner are knitted with a higher stitch per unit area or length than other sections of the liner. The liner may be knitted in a single layer or in multiple layers, wherein knitted layers are added on top of one another, in relation to a central axis of the tubular liner, so more layers make the material of the liner thicker. The multiple layers may vary in materials used and stitch density.

The materials and stitch density of the liner may also be varied either along the direction of the central axis of the liner, from the proximal end to the distal end, or in a circumferential direction, or a combination of both directions. The knitted structure may also include at least one solid section, wherein at least one knitted section is connected to the at least one solid section. The knitted and solid sections can be connected in many ways, such as molding, stitching, or using an adhesive.

The liner may have a welt, which may be an elastic band, connected to the proximal end of a knitted liner body, around the edge of the opening. The welt may vary in thickness or material and may be knitted or solid.

The knitted liner possesses advantages over known liners. Embodiments of the liner have a breathable interface, whereas most known liners placed next to the skin transferring high force do not breathe. Solid thickness silicone prosthetic liners or polyurethane prosthetic liners lack breathability.

Because the liner is knitted, design flexibility enables the form and structure of the eventual knitted liner to be rapidly changed. A liner knitted by machine permits manufacturing changes to occur rapidly. Custom manufacturing of an interface to measurements/digital scans is very attainable. Novel combinations with other materials and structures allows the optimization of the function and form of the knitted structure to every aspect of the person's needs.

The numerous advantages, features and functions of the embodiments will become readily apparent and better understood in view of the following description and accompanying drawings. The following description is not intended to limit the scope of the knitted interface, but instead merely provides exemplary embodiments for ease of understanding.

BRIEF DESCRIPTION OF THE DRAWINGS

Features, aspects, and advantages of the present disclosure will become better understood regarding the following description, appended claims, and accompanying drawings.

DETAILED DESCRIPTION OF VARIOUS EMBODIMENTS

A. Overview

A better understanding of different embodiments of the disclosure may be had from the following description read in conjunction with the accompanying drawings in which like reference characters refer to like elements.

While the disclosure is susceptible to various modifications and alternative constructions, certain illustrative embodiments are shown in the drawings and are described below in detail. It should be understood, however, there is no intention to limit the disclosure to the specific embodiments disclosed, but on the contrary, the intention is to cover all modifications, alternative constructions, combinations, and equivalents falling within the spirit and scope of the disclosure.

It will be understood that, unless a term is expressly defined in this patent to possess a described meaning, there is no intent to limit the meaning of such term, either expressly or indirectly, beyond its plain or ordinary meaning.

B. Various Embodiments of the Knitted Interface

Figures 1A, 1B:
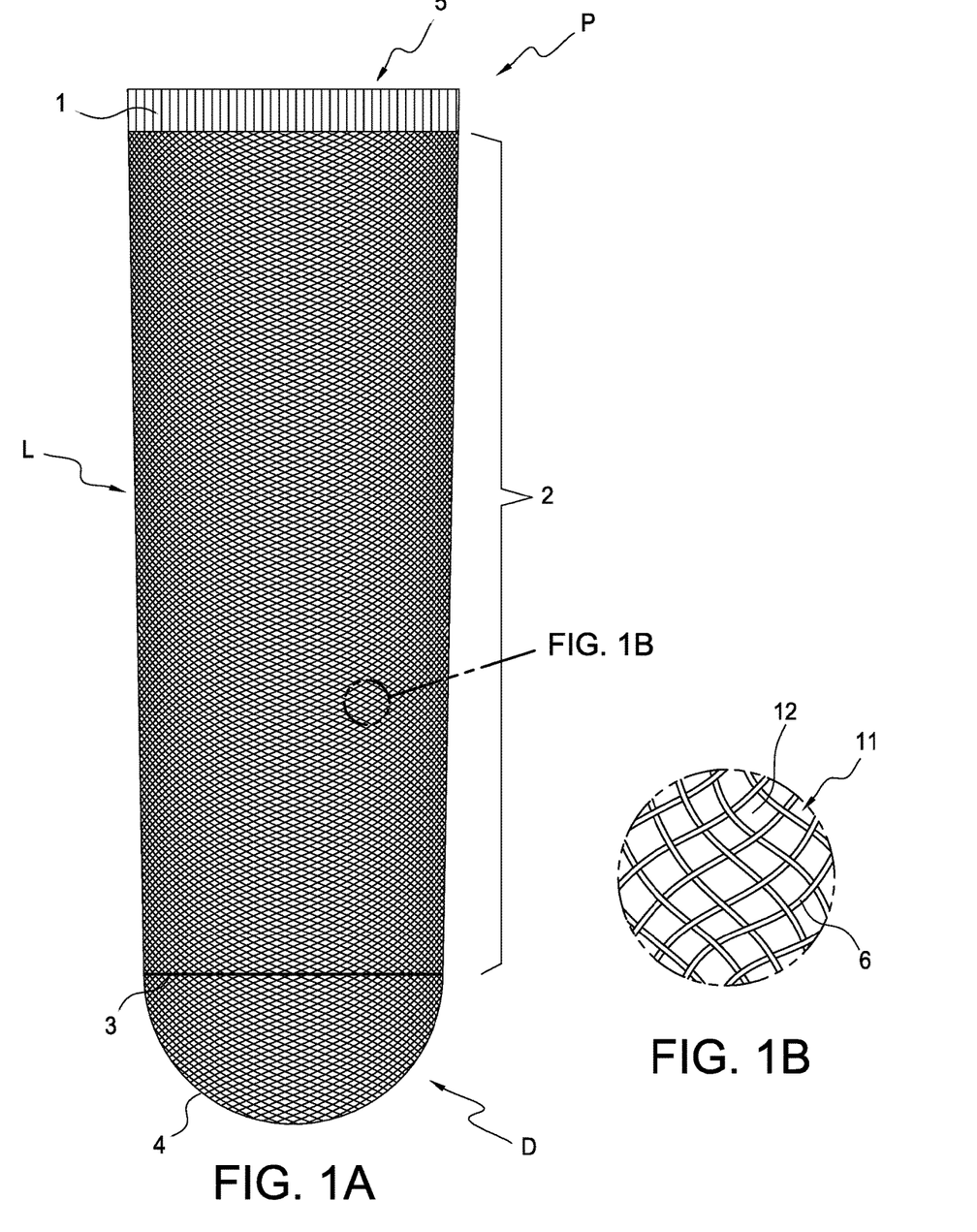
FIG. 1A is an elevational view of a knitted interface in the form of suspension liner.
FIG. 1B is a detail view from FIG. 1A showing a weave of the liner.
Figure 2:
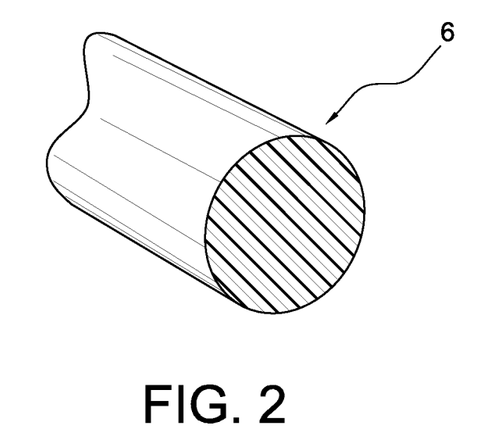
FIG. 2 is a cross-sectional perspective view of a solid elastomeric filament.

FIG. 1A illustrates a knitted interface in an exemplary form of a suspension liner L defined by a tubular body 2 having a proximal end P and a distal end D, knitted using elastomeric filaments 6, 7. An opening 5 at the proximal end P allows a residual limb to be inserted. The distal end D may have an opening, as it may be closed-ended or as a sleeve.

The liner L includes a welt 1 connected to the opening at the proximal end P of the liner L. The welt 1 comfortably provides a force on the residual limb to keep the liner L from slipping off or rolling down the limb when donned. While FIG. 1A shows the welt as being knitted to the tubular body 2, it may be connected in many other ways, including being stitched, molded, or adhered with an adhesive.

The welt 1 may be an elastic band located most proximally on the tubular body 2, connected to the proximal end P of the tubular body 2 around the edge of the opening 5. While the welt 1 may be preferably knitted with cotton filaments, it may be knitted with any suitable filaments, with many properties including elasticity such as combining the cotton filaments with elastane filaments. The filaments used to form the welt may differ from the filaments used to form the tubular body, and by be knitted therewith to secure the welt onto the tubular body. The welt may define a reinforced edge to the liner, and may have an elasticity that is greater than the tubular body to circumferentially tension about a limb, assisting in maintaining the liner about the limb.

The liner L in FIG. 1A also includes a seam 3 that may be used to close or finish the knitted structure of the tubular body 2 at the distal end D of the liner L. Other embodiments may have the seam located anywhere on the liner where it is advantageous to finish the knit or close the tubular body 2. Other embodiments may not require a seam to close the liner or finish the knit if closed knitting patterns that do not require seams are employed. Other ways of closing the liner L or finishing the knit, such as stitching or adhesives, may also be used.

The tubular body 2 of the liner has a knitted structure formed by knitted elastomeric filaments 6, 7, preferably silicone filament, but any elastomeric filament may be used, such as polyester, spandex, and so forth. Knitted elastomeric filaments provide a cushioned interface between a residual limb of a user and a prosthetic socket, while having frictional properties that help keep the residual limb from slipping or sliding within the socket.

The seam 3 may be formed by the same elastomeric filaments as forming the tubular body, in part to maintain the same desirable properties about the seam as in the remainder of the tubular body 2. Likewise, the welt 1 may be formed by the same elastomer filaments to likewise maintain the same desirable properties as the tubular body, however the welt may have a tighter knit structure to facilitate a reinforced edge about the tubular body to assure repeated donning and doffing of the tubular body.

FIG. 1A shows the tubular body 2 of the liner including solid chord silicone filaments 6. Solid chord filaments 6 are not hollow, as opposed to tube filaments 7, shown in FIG. 3, which are hollow.

Figure 3:
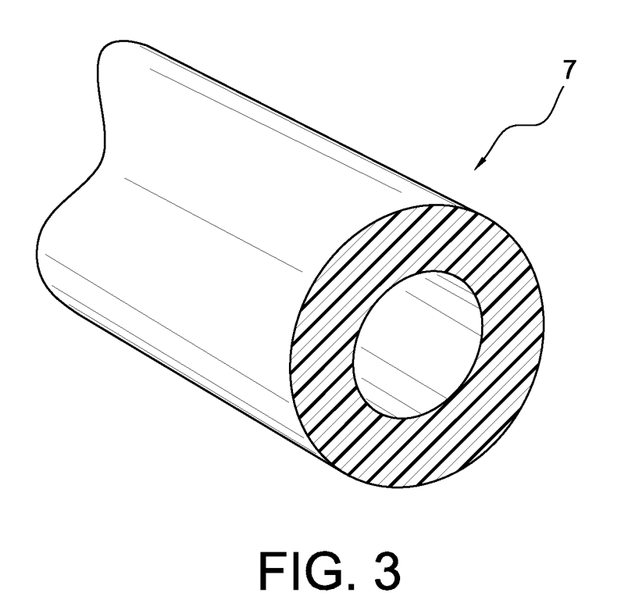
FIG. 3 is a cross-sectional perspective view of a hollow elastomeric filament.

In a variation, the tube filaments 7 can be inflated hydraulically or pneumatically to fill space between a residual limb and a prosthetic socket. The filaments may actively change and distribute pressure on the residual limb, and reduce shear forces on the skin of the limb, when the user is active. If silicon tubing is used in the knit it is possible that this tubing may be inflated (pneumatics/hydraulics) or deflated to control pressure distribution, volume of the interface/ amputees stump or temperature. If the knit contains two or more strands it can be controlled regarding inflation/deflation.

In one embodiment the system contains pressure sensors measuring the pressure in each strand and an actuator capable of increasing/decreasing pressure in each strand. Intelligent control of these fibers would permit intelligent distribution of pressure and temperature. In another embodiment, electronics are not used; pressure is redistributed to satisfy equilibrium in the system. This system would reduce peak pressures upon the interface and thereby decrease soft tissue breakdown in the underlying stump.

The tubular body 2 of FIG. 1A is knitted with filaments preferably made of only elastomeric material 6. Composite filaments may be used in other embodiments, wherein the filament is made of a combination of at least one elastomeric material and at least one textile-fabric, as shown in the cross-sectional views of the composite filaments illustrated in FIG. 4.

Figure 4:
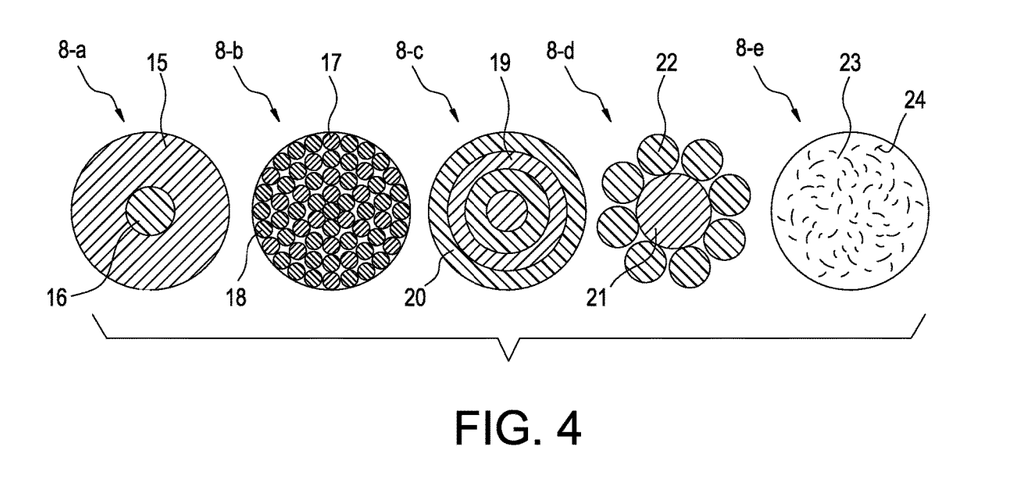
FIG. 4 are exemplary cross-sectional views of composite filaments according to an embodiment of the disclosure.

The different cross-sectional views 8a-e in FIG. 4 illustrate various composite filaments, but the combination of elastomeric and textile-fabric filaments is not limited to those illustrated therein. In these views 8a-8e, the location of the silicone or polymeric material portions 15 vary relative to textile material portions 16. View 8a illustrates a textile core 16, and a silicone outer portion 15. View 8b illustrates a mixture of silicone portions 17, and textile portions 18. An alternative would be to provide a soft inner portion with a lower durometer graduating to a firm outer portion with a higher durometer. View 8c shows an alternative of concentric silicone portions 19 and textile portions 20. View 8d depicts a multilayered combination with outer textile portions 22 and a silicone center portion 21. View 8e shows a silicone filament 23 with flocking 24.

The materials used in combination with the textile may be polymeric materials other than silicone. The material properties of the silicone can be modified by adding substances such as petroleum jelly or other lubrication. This permits the manufacturing process to be optimized (filaments may require lubrication in a knitting machine). This also permits clinical application to be optimized.

In an example, the filaments may have a Polyamide core or center portion (35%) and silicone outer portion (65%). Though any proportion of these materials can be utilized to suit a desired application. It is also possible to knit with silicone and solvron. Solvron is easily dissolvable in warm water leaving a 100% silicone structure.

Varying the composition and materials of the filament changes the material properties of the filaments and the knitted structure as a whole. Varying the knitted structure allows for optimization of certain properties of the liner, such as elasticity and frictional properties, to accommodate the various needs of the wearer.

The knitted structure of the liner enables combinations with other materials and structures, permitting the optimization of the function and form of the knitted structure to every aspect of the person's needs. For example, in a prosthetic application, the distal end D of a liner L can be principally silicone, this then transitions to a combination of silicone and polyamide, then over the knee elastomide is introduced to facilitate flexion of the knee, around the proximal aspect of the socket Kevlar is present (to protect from the proximal edge of the socket). The proximal aspect of the structure is such that it does not easily unravel and "roll-down" the leg.

The embodiment of FIG. 1A may be formed using different stitch densities. The distal portion 4 of the liner L may be knitted with a stitching density higher than the body 2, meaning there are more stitches per unit area or length than that of the tubular body 2. Other embodiments can be made with variable stitch densities wherein different areas of the liner are knitted with different densities. Different stitch densities cause the pressure applied to the liner from the residual limb and prosthetic socket to be distributed in different ways. It is therefore advantageous to vary knit densities to correspond to locations where pressures vary.

The tubular body 2 and distal portion D of the liner L in FIG. 1 are both knitted using a silicone filament. In other embodiments, many different filaments may be used, whether elastomeric or non-elastomeric. The filaments used may vary along the central axis of the tubular body 2 from proximal to distal ends, or may vary circumferentially, or a combination of the two. Varying the filament used can optimize the comfort and fit of the liner for the user. Often in form fitting or stretchy exercise clothing or undergarments, certain portions or bands within the clothing might be made of a more elastic material, a softer material, or a material that exhibits friction higher than the rest of the garment. These varied materials within a garment can provide extra comfort to more sensitive areas of the body and a more secure fit without slipping, such as form fitting exercise pants with elastic bands at the waist, knee, and ankle, to keep the pants from slipping or migrating up or down the legs of the wearer. The same strategy may be employed in the formation of the knitted interface to maximize user comfort and garment stability.

In other embodiments, knitted sections of the liner can be combined with solid sections of the liner, such as molded silicone or any other solid material that can be connected to the knitted portion of the liner. A solid material here includes any suitable material that is not knitted, or a non-knitted material.

Figure 5:
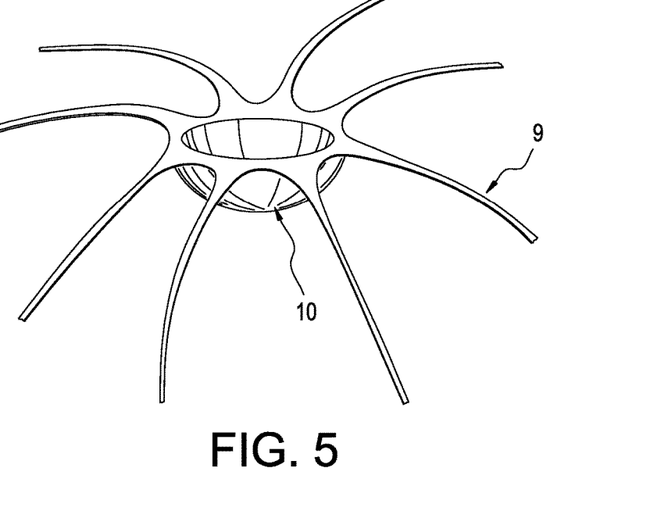
FIG. 5 is a schematic view of a distal end section having filament extrusions

An embodiment of combining a solid section with a knitted section of the interface is shown in FIG. 5, showing a solid polymeric portion 10 with filament extrusions 9. The filament extrusions 9 can then be the filament to knit the knitted section of the liner, such as the tubular body 2.

Various materials and methods to combine knitted portions of the interface with solid portions of the interface may be used. Using the embodiment of FIG. 5, the distal end section of a liner is made from a solid non-breathing polymeric material, such as silicone. This solid polymeric material portion 10 has multiple long extrusions 9 extending therefrom (similar in appearance to a Jelly fish). These extrusions are then knitted with other filaments 9 or suitable yarns or filaments for created the knitted interface. This embodiment allows for the advantages of both a solid polymer section for stability, and knitted polymeric filaments for breathability. Another method of achieving this would be to take a knitted structure and inject/apply polymeric material to it such that a solid section/pieces are formed.

Figure 6:
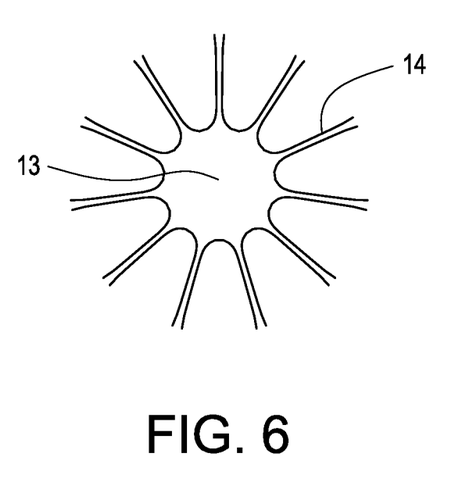
FIG. 6 is a schematic view of another embodiment a polymeric piece having filament extrusions.

FIG. 6 illustrates another embodiment including one or more pieces of polymeric material "pieces" 13 having multiple filament extrusions 14 extending therefrom. These pieces 13 could be used for cushioning over a fibular head. These pieces 13 provide the function of having different functions to a "main" knitted structure, being softer, or more rigid, or having different stretch properties. Again the "reverse" can be achieved by taking a knitted structure and applying/injecting silicone to it such that solid sections/regions are attained.

The preferred embodiment in FIG. 1 is knitted with only one layer of knitted elastomeric filament. The knit may also include multiple layers of knitting, wherein knitted layers are added on top of one another, or outwardly relative to the central axis of the tubular body 2, to vary the material thickness of the interface. Each of these layers may be knitted using different knitting densities, materials, knitting patterns, and knitting thicknesses, and may be adhered, knitted or otherwise secured to one another.

FIG. 1B shows a knitted structure of the liner L whereby the filaments 6 are knitted in a knitted structure or mesh 11 having interstices 12, that may shift during wear depending on the tightness of the knitted structure. If desired for a highly breathable liner, the knitted structure, as in the density of the structure, is looser or the interstices are larger than in a tighter knitted structure whereby the filaments are more tightly knitted with one another.

According to the manufacture processes, the tightness of the knit can be adjusted either over the entire liner or varied at locations of the liner. The distal end may have a tighter knitted structure as the limb may taper at such location, and may have a relatively looser knitted structure about the proximal end whereby the limb may be wider. With a looser structure, the knitted structure may yield more to the shape of the limb upon which it is worn due to movement of the user or radial distension of the knitted interface. Further, because the filaments 6, when silicone or other elastomeric material, are generally elastic, the liner can stretch over the limb of the user.

In another embodiment, a thermoformable filament may knit the liner, which is pliable to knit during manufacturing, yet when exposed to high temperature becomes rigid. This permits part or all of the structure to become rigid or semi-rigid and allows the potential loading properties of the liner to be manipulated. A blended version of silicone and thermoformable filaments can permit a silicone interface that can be molded to a user's residual limb using low heat.

The silicone/gel knitted fibers or filaments may be blended with a range of other textiles/materials. For example, the proximal end could be Lycra/cotton/polyester fibers, and blended/knitted into the silicone knit. This would allow the proximal aspect of the interface to fit snugly and comfortably about a joint (knee or hip) and the silicone aspect to address pressure distribution/shear issues commonly in a residual limb. Blending can be achieved by using an extrusion which begins with silicone and transitions to other material. Blending occurs within the heterogeneous filament. Blending can also be achieved by the knitting pattern. Homogenous filaments may be blended in the structure. Further-still, a non-elastic matrix, as taught in prior art references incorporated, can be knitted into the silicone knitted structure.

The liner described is worn by the wearer so it is in direct contact with the wearer, acting as an interface between the wearer and another liner, such as a brace, splint, or prosthetic liner. The liner described above is donned by the wearer so the liner covers, and is in direct contact, with a residual limb of the wearer. A prosthetic socket is then placed over the liner and residual limb, the liner acting as an interface between the residual limb and the prosthetic socket.

The liner formed using a knitted elastomeric filament offers numerous advantages over current interfaces. The silicone used to knit the liner described above exhibits material properties desirable for contact with the skin of the wearer.

Silicone is durable and flexible, soft on the skin and smooth to the touch. It can withstand up to 1800 psi and extruded filaments can achieve up to 800 percent elongation. Its desirable frictional qualities provide for better soft tissue stabilization than other materials used in liners, which reduces shear forces put on the skin by the prosthetic socket. Silicone has good resistance to weathering, compression, fatigue and flexing, and good cut growth resistance. These are all important factors as it is desirable to use the interfaces in all conditions, weather, and climates.

Having an interface formed by knitted silicone embodies the same or enhanced qualities already mentioned, and additional qualities desired for such an interface. A knitted silicone interface provides more flexibility than a solid one because both the knitted pattern and the filaments themselves can expand. The knitted interface can stretch non-uniformly, depending on the contour of the surface of the residual limb, to further enhance shear stress relief on the skin.

Because silicone is hydrophobic, the knitted silicone filaments wick moisture away from the skin of the wearer due to the porous nature of the knitting pattern. Because of this, a knitted silicone structure breathes much better than other solid liners. Active skin care ingredients can be incorporated into silicone, as described in U.S. Pat. No. 7,459,598 B2, granted Dec. 2, 2008, incorporated herein in its entirety by reference, which then migrates to the surface of the material and interact with the skin. For example, Aloe-Vera can be incorporated to soften the appearance of scar tissue and reduce skin irritation, and Vaseline, which assists with skin hydration. Other ingredients that promote healthy, strong skin and control other dermatological problems may also be incorporated into the silicone. Silicone is highly biocompatible and can be worn over wounds without the skin reacting negatively.

There are also benefits to using silicone outside of its interaction with the skin of the wearer. Silicone is odorless and environmentally friendly. It is easily trimmed to fit the size of a residual limb and both the diameter of the filaments and the durometer of the material can vary widely depending on the patient's needs. The hardness of solid silicone chord filaments may range from 25 to 80 durometer and the diameter may range from less than about 6 mm to about 30 mm, depending on the durometer. Silicone possesses excellent bonding qualities and is easily molded and extruded, which is important when a small diameter is needed to produce filaments small enough to knit with.

As discussed, weaving, crocheting, knitting, purling or other methods can be used with the polymeric filaments creating an interface structure from long extrusions/filament. The "tightness" of weave or knitted structure may be adjusted or changed to modify the properties of the interface, and may be variable. The filaments may have a solid (cord) or hollow (silicone tubing) structure. Circular, rectangular, or any other shape in cross sections may be used (depending upon the desired characteristics of the interface), or may be of fixed section or variable cross-section.

The knitted interface is of particular interest at the junction between person and an external object/device worn for extended periods of time, as it permits both comfortable distribution of forces and breathability. In prosthetics, the interface between prosthesis and person, may be a knitted liner placed between the skin and a traditional prosthetic liner. The knitted liner between skin and prosthetic socket is a replacement/improvement to current traditional prosthetic liners. This knitted liner may utilize a range of suspension methods pin, lanyard, vacuum (if parts of it are air-tight). In orthopedics, the interface may be used between brace/orthosis and person, as padding or migration control.

The knitted interface may comprise an orthopedic device, such as in a compression sleeve or other type of compression based orthopedic device. A diabetic sock may be constructed from knitted silicone to decrease shear forces, increase protection of the skin, and decrease probability of foot ulceration. In a similar use, a partial foot sock may be a knitted silicone sock with integrated toe-filler providing protection and cushioning for the remaining limb.

The knitted interface may be used for burn victims by providing a protective layer over sensitive skin. In another use, a hospital mattress may incorporate the knitted interface by being soft and breathable to decrease the incidences of pressure sores.

The described embodiments do not require that all the advantageous features and advantages be incorporated into every embodiment. While the foregoing embodiments have been described and shown, it is understood that alternatives and modifications of these embodiments, such as those suggested by others, may be made to fall within the scope of the disclosure.

The invention claimed is:

1. A knitted interface, comprising:
a knitted structure defining a sleeve and formed entirely from a plurality of elastomeric polymer filaments having a plurality of interstices permitting transfer of air therethrough;
wherein the elastomeric polymer filaments are composite filaments comprising portions formed by elastomeric materials and textile-fabric materials;
wherein the plurality of elastomeric polymer filaments of the sleeve are integrally formed with a solid distal end portion.

2. The knitted interface of claim 1, wherein the elastomeric polymer filaments are formed from silicone.

3. The knitted interface of claim 1, wherein the elastomeric polymer filaments have a hollow cross-section.

4. The knitted interface of claim 1, wherein the knitted structure has a variable stitch density.

5. The knitted interface of claim 1, wherein the interstices vary in shape and size according to a stitch density of the knitted structure upon movement or radial distension of the knitted interface.

6. The knitted interface of claim 1, wherein the elastomeric polymeric filaments are hydrophobic.

7. The knitted interface of claim 1, wherein the knitted structure consists of the elastomeric polymeric filaments.

8. The knitted interface of claim 1, wherein the knitted structure forms a tubular body constructed by the knitted structure.

9. The knitted interface of claim 8, further comprising a welt knitted about a first end of the tubular body forming an opening being reinforced relative to a remainder of the tubular body.

10. The knitted interface of claim 9, wherein the welt is formed by filaments having properties different from the elastomeric polymeric filaments and knitted therewith.

11. The knitted interface of claim 8, further comprising a seam closing a second end of the tubular body, the seam being formed by elastomeric polymeric filaments.

12. The knitted interface of claim 1, wherein the knitted structure includes a combination of the elastomeric polymeric filaments knitted with textile filaments.

13. The knitted interface of claim 1, wherein the elastomeric polymeric filaments comprise at least one solid polymeric material portion forming a distal end section and multiple long extrusions extending from a proximal edge of the distal end section for being knitted with other extrusions or filaments.

14. The knitted interface of claim 1, wherein the portions formed by elastomeric materials and textile-fabric materials are coextensive along substantially an entirety of an axial length of the composite filaments.

15. A knitted interface, comprising:
a knitted structure formed from a plurality of elastomeric polymer filaments having a plurality of interstices permitting a transit of air therethrough;
wherein the elastomeric polymer filaments are formed from silicone and have a solid cross-section;
wherein the interstices vary in shape and size according to a stitch density of the knitted structure upon movement or radial distension of the knitted interface;
wherein the elastomeric polymer filaments comprise first and second layers coextensive with each other, the first layer having a lower durometer than the second layer;
wherein the elastomeric polymer filaments comprise at least one additional substance selected from the group consisting of petroleum jelly and a lubrication substance.

16. The knitted interface of claim 15, wherein the knitted structure consists of the elastomeric polymeric filaments.

17. The knitted interface of claim 15, wherein the knitted structure includes a combination of the elastomeric polymeric filaments knitted with textile filaments.

18. The knitted interface of claim 15, wherein the knitted structure has a variable stitch density.

19. A knitted interface comprising:
a knitted structure defining a sleeve and formed entirely from a plurality of elastomeric polymer filaments having a plurality of interstices permitting transfer of air therethrough;
a solid distal end portion integrally formed with the plurality of elastomeric polymer filaments;
the plurality of elastomeric polymer filaments defining a variable stitch density across portions of the sleeve;
the knitted structure defining at least one solid section connected to the knitted structure and within the sleeve;
at least two coextensive layers defined in the sleeve and formed of the plurality of elastomeric polymer filaments, each of the at least two coextensive layers defined in the sleeve having a different density;
the interstices vary in shape and size according to a stitch density of the knitted structure upon movement or radial distension of the knitted interface;
wherein the elastomeric polymer filaments are composite filaments comprising portions formed by elastomeric materials and textile-fabric materials;
wherein each of the composite filaments defines at least two discrete textile-fabric portions and at least two discrete elastomeric portions;
wherein the composite filaments define a first layer and a second layer coextensive with each other, the first layer having a lower durometer than the second layer;
wherein the composite filaments further comprise at least one additional substance selected from the group consisting of petroleum jelly and a lubrication substance.

* * * * *